US009505788B2

(12) United States Patent
van der Kruijs et al.

(10) Patent No.: US 9,505,788 B2
(45) Date of Patent: Nov. 29, 2016

(54) PROCESS TO PREPARE ALUMINOXANES BY REACTION OF ALKYLALUMINUM WITH ALLYLIC ALCOHOLS

(71) Applicant: Akzo Nobel Chemicals International B.V., Arnhem (NL)

(72) Inventors: Peter van der Kruijs, Deventer (NL); Jelle Martin Bergsma, Deventer (NL); Richard Herman Woudenberg, Diepenveen (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/032,368

(22) PCT Filed: Oct. 24, 2014

(86) PCT No.: PCT/EP2014/072807
§ 371 (c)(1),
(2) Date: Apr. 27, 2016

(87) PCT Pub. No.: WO2015/062977
PCT Pub. Date: May 7, 2015

(65) Prior Publication Data
US 2016/0272658 A1 Sep. 22, 2016

(30) Foreign Application Priority Data
Oct. 28, 2013 (EP) ..................................... 13190471

(51) Int. Cl.
C07F 5/06 (2006.01)
B01J 31/14 (2006.01)

(52) U.S. Cl.
CPC .............. *C07F 5/068* (2013.01); *B01J 31/143* (2013.01); *B01J 2231/12* (2013.01); *B01J 2231/20* (2013.01)

(58) Field of Classification Search
CPC .................................... C07F 5/06; C08F 4/00
USPC ......................................................... 556/27
See application file for complete search history.

(56) References Cited

U.S. PATENT DOCUMENTS

| | | | |
|---|---|---|---|
| 5,663,394 | A | 9/1997 | Roberg et al. |
| 5,670,589 | A | 9/1997 | Geerts et al. |
| 5,777,143 | A | 7/1998 | Malpass et al. |
| 5,831,109 | A | 11/1998 | Smith et al. |
| 6,124,229 | A | 9/2000 | Becker et al. |
| 2012/0071679 | A1 | 3/2012 | Fang et al. |
| 2013/0211018 | A1 | 8/2013 | Willocq et al. |

FOREIGN PATENT DOCUMENTS

| | | | | |
|---|---|---|---|---|
| DE | 2507532 A1 | * | 8/1975 | ............... A61K 8/58 |
| EP | 1264847 A1 | * | 12/2002 | ............... C08F 10/00 |
| EP | 2119732 A1 | | 11/2009 | |
| JP | 48-12080 | | 4/1973 | |
| JP | 03-271295 A | | 12/1991 | |
| WO | 97/23288 A1 | | 7/1997 | |
| WO | 2007/076398 A2 | | 7/2007 | |
| WO | 2012/122332 A1 | | 9/2012 | |
| WO | 2014/105614 A1 | | 7/2014 | |

OTHER PUBLICATIONS

El-Ichi et al., Tetrahedron Letters, 22(38), 1981, 3737-3740.*
International Preliminary Report on Patentability; PCT/EP2014/072807; Jan. 11, 2016.*
European Search Report for European Serial No. 13190471.6, date Mar. 17, 2014.
International Search Report and Written Opinion for PCT/EP2014/072807, date of mailing Feb. 3, 2015.
Enzo Giannetti et al., Homogeneous Ziegler-Natta Catalysis. II. Ethylene Polymerization by IVB Transition Metal Complexes/Methyl Aluminoxane Catalyst Systems, Journal of Polymer Science: Polymer chemistry Edition, vol. 23, 2117-2133 (1985).
Rainer Glaser et al., Thermochemistry of the Initial Steps of Methylaluminoxane Formation. Aluminoxanes and Cycloaluminoxanes by Methane Elimination from Dimethylaluminum Hydroxide and its Dimeric Aggregates, Journal of the American Chemical Society, 2011, pp. 13323-13336.
Hideaki Hagihara et al., Copolymerization of Propylene and Polar Allyl Monomer With Zirconocene/Methylaluminoxane Catalyst: Catalytic Synthesis of Amino-Terminated Isotactic Polypropylene, American chemical Society, 2004, pp. 5145-5148.
Pasynkiewicz et al., Reactions of Trimethylaluminium With 2-[methyl-bis(trimethylsiloxy)silyl]but-2-ene-1,4-diol: synthesis and structure of $[Al(CH_3)]$-$[OCH_2(SiMe(OSiMe_3)_2)C=C(H)CH_2O]_2[Al(CH_3)_2]_2$, Journal of Organometallic Chemistry, 437, 1992, pp. 99-110.
Pasynkiewicz, Reactions of Organoaluminium Compounds With Electron Donors, Institute of Organic Chemistry and Technology, Technical University, Warsaw Poland, pp. 509-521.

(Continued)

*Primary Examiner* — Porfirio Nazario Gonzalez
*Assistant Examiner* — Kofi Adzamli
(74) *Attorney, Agent, or Firm* — Alice C. Su

(57) ABSTRACT

The present invention relates to a process to prepare alkylaluminoxanes by reaction of alkylaluminium with a substituted allylic alcohol of the formula wherein each R1 and R2 independently are an aliphatic or aromatic hydrocarbon group, and R3, R4, and R5 each independently may be the same hydrocarbon group as R1 and R2 or a hydrogen atom in the presence of an inert organic solvent. Additionally, it relates to the alkylaluminoxanes obtainable by the above process and their use.

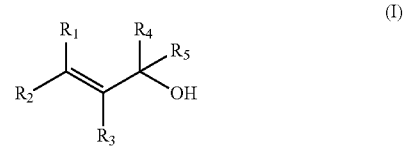

(I)

15 Claims, No Drawings

(56) References Cited

OTHER PUBLICATIONS

Ei-ichi Negishi et al., Scope of the Palladium-Catalyzed Coupling Reaction of Organometallics With Allylic Electrophiles, Effect of the Leaving Group, Tetrahedron Letters, vol. 22, No. 38, pp. 3737-3740 (1981).

Madri Smit et al., Effects of Methylaluminoxane Immobilization on Silica on the Performance of Zirconocene Catalysts in Propylene Polymerization, Journal of Polymer Science, Part A: Polymer Chemistry, vol. 43, pp. 2734-2748 (2005).

Jouni Turunen et al., NMR Studies on the Reactivity of Aluminium Compounds With an Unsaturated Alcohol, Journal of Molecular Catalysis A: Chemical 123, 1997, pp. 35-42.

Hergen Winter, The Preparation of Aluminoxane From Trimethylaluminium at a Defined Surface of Deeply Cooled Ice, Hüthig & Wepf Verlag, Zug, 1995, pp. 119-125.

* cited by examiner

PROCESS TO PREPARE ALUMINOXANES BY REACTION OF ALKYLALUMINUM WITH ALLYLIC ALCOHOLS

This application is a national stage filing under 35 U.S.C. §371 of PCT/EP2014/072807, filed Oct. 24, 2014, which claims priority to European Patent Application No. 13190471.6, filed Oct. 28, 2013, the contents of which are each incorporated herein by reference in their entireties.

The present invention relates to a novel process to prepare aluminoxanes.

Aluminoxanes are known in the industry, mainly by their application as a catalyst component in polymerization catalysts, especially as a co-catalyst in metallocene catalysts that are used in polymerizing or oligomerizing olefins.

Aluminoxanes (also sometimes referred to as alumoxanes) may be linear, cyclic, oligomeric or polymeric structures wherein two or more aluminium atoms are linked via an oxygen bridge. For example, they have structures like R(—Al(—R)—O)$_n$—Al—R$_2$), wherein n is an integer, each R can independently be an alkyl or alkoxy group, and optionally two or more of the R groups may be linked together to give the indicated cyclic structures, i.e., two R groups can be an oxygen bridge between two aluminium atoms. When at least part of the R groups are methyl groups, the aluminoxane is called a methylaluminoxane (MAO).

Aluminoxanes are described in several documents such as in R Glaser et al., "Thermochemistry of the Initial Steps of Methylaluminoxane Formation. Aluminoxanes and Cycloaluminoxanes by Methane Elimination from Dimethylaluminum Hydroxide and Its Dimeric Aggregates", *JACS*, 2011, 133, 13323-13336; H. Sinn et al., "Ziegler-Natta Catalysis", *Advances in Organometallic Chemistry*, Volume 18, 1980, pp. 99-149; T Sugano et al., "Characterization of alumoxanes by $^{27}$Al-NMR spectra", *Journal of Molecular Catalysis*, Volume 82, Issue 1, 11 Jun. 1993, pp. 93-101; E Gianetti et al., "Homogeneous Ziegler-Natta Catalysis. II. Ethylene polymerization by IVB transition metal complexes/methyl aluminoxane catalyst systems", *Journal of Polymer Science: Polymer Chemistry Edition*, Volume 23, Issue 8, pp. 2117-2134, August 1985; and S. Pasynkiewicz, "Alumoxanes: Synthesis, structures, complexes and reactions", *Polyhedron*, Volume 9, Issues 2-3, 1990, pp. 429-453.

U.S. Pat. No. 5,663,394 discloses a process to prepare methylaluminoxanes. The process involves the reaction of trimethylaluminium with water in an organic solvent. Because of the uncontrollable reactivity of trimethylaluminium with water (also described by H Winter in "The preparation of aluminoxane from trimethylaluminium at a defined surface of deeply cooled ice" in *Macromol. Symp.* 97, 119-125 (1995)), the water reactant can only be underdosed and the reaction in the first instance gives a low conversion. The document in the Examples mentions dosing water in about 0.2 molar ratio to the amount of trimethylaluminium. The process as described in the above U.S. Pat. No. 5,663,394 patent involves an additional step of recycling unreacted trimethylaluminium together with solvent and so concentrating the obtained aluminoxane. At the same time, the reaction between water and trimethylaluminium not only gives the desired aluminoxanes but is also known to give some aluminium salts, like aluminium hydroxide and aluminium oxides, that will precipitate, and gel formation. The gel formation and precipitation problems are known to get worse when TMAL and H$_2$O are dosed closer to equimolar as would be desirable from a reaction yield point of view, and it should be noted that by underdosing the water reactant and the several recycling and concentration steps the above US patent attempts to avoid these problems as much as possible.

The present invention provides an improved process to prepare alkylaluminoxanes with high yield and high conversion that does not require the recycling and separation steps as described for the above state of the art process. In addition, the process of the present invention can be performed in higher concentration, i.e. it can be performed in lower amounts of solvent.

The invention now provides a process to prepare alkylaluminoxanes by reaction of alkylaluminium with a substituted allylic alcohol of the formula

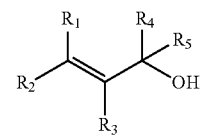

wherein each R1 and R2 independently are an aliphatic or aromatic hydrocarbon group, and R3, R4, and R5 each independently may be the same hydrocarbon group as R1 and R2 but may also be a hydrogen atom in the presence of an inert organic solvent.

The invention in addition provides the alkylaluminoxanes obtainable by the above process and their use as a component in catalysts used for olefin polymerization or oligomerization processes, such as processes to prepare polyethylene, polypropylene or rubber. The catalyst in which aluminoxane is used can be a homogeneous or heterogeneous catalyst with or without a support or carrier.

The use of alcohols, ketones, and carboxylic acids in preparing aluminoxanes has been described in U.S. Pat. No. 5,831,109. No alcohols are exemplified, but it is disclosed that they have the structural formula ROH wherein R is alkyl or aryl. Consequently, no allylic alcohols are disclosed in this document.

In the present invention it was found that when reacting alkylaluminium with alcohols of the above specific substituted allylic type, the reaction to give aluminoxanes is gentle and can be better controlled than with water and therefore the alcohol reactant that will deliver the oxygen can be dosed in higher ratio (than water) to give an improved yield and a lower amount of side products. At the same time, the reaction was found to be not so slow that a lot of energy needs to be added to make it progress. In other words, the present invention provides a process to prepare aluminoxanes with a balanced reactivity between the starting materials. Apart from that, both the aluminium and the oxygen delivering reagents can be present in a higher amount in the reaction mixture, or to phrase it differently, less solvent needs to be used.

The process of the invention is favourable as it indeed leads to higher conversion, does not require the same number of after-treatment steps like recycling unreacted starting materials and significant amounts of solvent, and also does not require a separation step to remove undesired side products or unreacted reagents.

As an additional advantage, the reaction of the present invention, when compared to using alcohols that are not allylic alcohols according to the invention, was found to proceed under much milder conditions such as a lower temperature. Because the substituted allylic alcohols of the present invention react with alkylaluminium in the reaction to prepare aluminoxanes under milder conditions, the reaction is characterized by a better yield, higher conversion, and less side product formation than with other alcohols, or water.

For example, when comparing the use of prenol, which is a substituted allylic alcohol of the present invention, with tert butanol or allyl alcohol (i.e. wherein all groups R1 to R5 are a hydrogen atom, 2-propene-1-ol), it was established that tert. butanol needs several hours of heating to about 100° C. before a decent conversion is obtained and that the reaction with allyl alcohol does not proceed at all.

It should be noted that U.S. Pat. No. 5,670,589 also discloses a reaction of aluminium-containing metalorganic materials with alcohols containing an unsaturated carbon-carbon bond. However, in this document only reactions of aluminoxanes with non-allylic unsaturated alcohols are described. EP1264847 discloses in Example 11 a reaction of an alkylaluminium and allyl alcohol. Allyl alcohol is not a substituted allylic alcohol as covered by the present invention and moreover the product made by EP'847 is not an aluminoxane with at least one Al—O—Al unit in its structure. The same goes for DE 2507532 and El-ichi Negishi et al., "Scope of the palladium catalyzed coupling reaction of organometallic with allylic electrophiles. Effect of the leaving group", *Tetrahedron Letters*, Vol. 22, No. 38, 1981, pp. 3737-3740, which documents also relate to aluminium-containing molecules that do not possess the Al—O—Al functionality in their structure possessed by aluminoxanes as defined to be the object of the present invention.

It should be additionally noted that S. Pasynkiewicz and W. Ziemkowska in "Reactions of trimethylaluminium with 2-[methylbis(trimethylsiloxy)silyl]but-2-ene-1,4-diol: synthesis and structure of [Al(CH$_3$)]—[OCH$_2$(SiMe(OSiMe$_3$)$_2$)C═C(H)CH$_2$O]$_2$[Al(CH$_3$)$_2$]$_2$" in *Journal of Organometallic Chemistry*, 437 (1992) 99-110 disclose the reaction of trimethylaluminium with an allylic alcohol wherein R is bis (trimethylsiloxy) silyl. This allylic alcohol is different from those of the present invention and moreover the reaction product formed in this document is not an aluminoxane as described in the introduction of this patent (the formed products do not possess an Al—O—Al covalent bonds-containing structure) nor an aluminoxane recognized as a catalytically active component.

The invention in addition in a preferred embodiment relates to a process to prepare alkylaluminoxanes by reaction of alkylaluminium with a substituted allylic alcohol of the formula

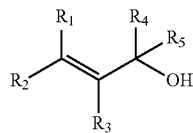

wherein each R1 and R2 independently are an aliphatic or aromatic hydrocarbon group, and R3, R4, and R5 each independently may be the same hydrocarbon group as R1 and R2 or a hydrogen atom
in the presence of an inert organic solvent containing a carrier, and to the supported aluminoxanes obtainable by this process.

The advantages of the above process and products are that the formed carrier-supported aluminoxanes are more storage stable and less susceptible to gelling. This leads to further advantages when the aluminoxanes need to be further processed later.

In preferred embodiments the substituted allylic alcohol is of the formula

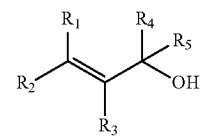

wherein each R1 and R2 independently are a branched or unbranched alkyl or alkylene group, more preferably an alkyl or alkylene group of up to 20 carbon atoms, and R3, R4, and R5 each independently may be the same alkyl or alkylene group as R1 and R2 but may also be a hydrogen atom. Most preferred are substituted allylic alcohols wherein R4 and R5 are a hydrogen group.

More preferred substituted allylic alcohols are 3-methyl-2-pentene-1-ol, 4-methyl-3-pentene-2-ol, 3-methyl-2-hexene-1-ol, 3-ethyl-2-pentene-1-ol, (trans)-3,7-dimethyl-2,6-octadien-1-ol (geraniol), and 3-methyl-2-butene-1-ol (prenol). Most preferred is prenol.

In preferred embodiments, the alkylaluminium is a trialkylaluminium wherein the alkyl substituents are alkyl groups of up to 8 carbon atoms, more preferably isobutyl, ethyl or methyl. Even more preferred alkylaluminium compounds are compounds wherein at least 50%, even more preferably at least 80% of the alkyl groups are methyl, like most preferably trimethylaluminium.

In the process of the invention the ratio of reactants in one embodiment can be about 0.1 to 0.8 molar equivalent of substituted allylic alcohol on 1 equivalent of alkylaluminium reactant; preferably, however, it is between 0.5 and 0.8 molar equivalent, more preferably between 0.6 and 0.75 molar equivalent.

The alkylaluminium in some embodiments of the process is present in an amount of about 1.5 to 20 wt. % aluminium on total reaction mixture, which when using trimethylaluminium corresponds to between about 4 and 54 wt. % trimethylaluminium on total reaction mixture. Preferably, the amount of alkylaluminium is between 5 and 20 wt. %, more preferably 5 and 14 wt. %, on total reaction mixture.

As already indicated above, this means that significantly less solvent needs to be used in the process of the invention when compared to state of the art processes, though it is of course also possible to use more solvent and remove or evaporate it later.

In yet another preferred embodiment of the processes of the invention, in a first step the substituted allylic alcohol is dosed to a trialkylaluminium solution in inert solvent, which is next dosed to a suspension of inert solvent optionally containing a carrier, after which further alkylaluminium is added and the resulting reaction mixture (suspension) undergoes a heat treatment.

In a more preferred embodiment in the first step the molar ratio between substituted allylic alcohol and trialkylaluminium is between 0.9:1 and 1:0.9 and the additional alkylaluminium that is added is in a molar amount of between 0.2 and 0.6 mole % on the basis of total substituted allylic alcohol, preferably ending with a total molar ratio of alcohol on aluminium between 0.6 and 0.75 molar equivalent as indicated above.

In yet another preferred embodiment, the process is operated in the presence of aluminoxane, optionally in a continuous or semi-continuous mode. Even more preferably, the process involves first preparing an alkoxide addition product of the substituted allylic alcohol and the alkyl aluminium in an inert organic solvent and (semi-continuously or continuously) adding or dosing this adduct to—previously formed—aluminoxane in an inert organic solvent optionally containing a carrier, or vice versa, though adding or dosing aluminoxane to the adduct is less preferred because it may then be harder to control the reaction. Because the aluminoxane acts as a catalyst in the reaction towards producing (more) aluminoxane, this way of performing the process of the invention is very favourable. Also, performing the reaction this way ensures that the exothermic nature of the reaction can be much better controlled.

As the skilled person will be aware, suitable reaction temperatures during the process are dependent on the choice of starting materials. They are suitably between 0° C. and reflux, in a preferred embodiment between 0 and 100° C., more preferably between 0° C. and 80° C., even more preferably between 10 and 50° C., and most preferably between 20 and 40° C.

However, when a carrier is present, during the process the reaction mixture is preferably heated to a temperature of higher than 80° C., even more preferably higher than 90° C. In one embodiment the temperature preferably is less than 200° C. An even more preferred way of performing the process in the presence of a carrier is refluxing the mixture in the inert organic solvent.

The inert organic solvent in which the process of the present invention is performed can be any organic hydrocarbon solvent that the skilled person knows is not reactive with an alkylaluminium compound. Examples thereof are alkanes, such as heptanes, hexanes, or aromates, such as toluene, xylene, ethylbenzene, cumene, mesitylene. Preferably, the solvent is toluene. With inert solvents it is intended to also exclude solvents that are capable of complexing with the aluminium-containing reactants, examples of which are solvents containing an oxygen or nitrogen atom, like ethers such as tetrahydrofuran.

Examples of the carrier include inorganic or organic support materials, which may be a porous support materials and the aluminoxane may be adsorbed or absorbed therein or thereon. Non-limiting examples of suitable supports include compounds comprising Groups 2, 3, 4, 5, 13, and 14 oxides and chlorides. Suitable supports may include, for example, silica, magnesia, titania, zirconia, montmorillonite, phyllosilicate, alumina, silica-alumina, silica-chromium, silica-titania, magnesium chloride, graphite, magnesia, titania, zirconia, and the like. Combinations of supports may also be suitable, including, for example, silica-chromium, silica-alumina, silica-titania, and the like. In one embodiment, fumed or calcined silica is a suitable support. The support may possess an average particle size in the range of from about 0.1 to about 90 µm, or from about 1 to about 40 µm, or from about 5 to about 40 µm The support, such as an inorganic oxide, may have a surface area in the range of from about 10 to about 700 m2/g, a pore volume in the range of from about 0.1 to about 4.0 cc/g, and an average particle size in the range of from about 1 to about 500 µm. In some embodiments, the support may have a surface area in the range of from about 50 to about 500 m2/g, a pore volume of from about 0.5 to about 3.5 cc/g, and an average particle size of from about 10 to about 200 µm. In some embodiments, the support may have a surface area in the range of from about 100 to about 400 m2/g, a pore volume from about 0.8 to about 3.0 cc/g, and an average particle size is from about 5 to about 100 µm. In some embodiments, the average pore size of the support may be from about 1 to about 50 µm. In some embodiments, the average pore size of the support may be in the range of from about 10 to about 1000 Å, of from about 50 to about 500 Å, or from about 75 to about 350 Å.

The invention is illustrated by the (comparative) Examples below.

EXAMPLES

Comparative Example 1

Allyl Alcohol as Reactant

A 30 ml glass vial equipped with a magnetic stirring bar was charged with 6.1 g toluene and 2.7 g (37.5 mmol) trimethylaluminium (ex AkzoNobel). To this solution, 0.44 g (7.5 mmol) of allyl alcohol (ex Baker) was slowly added, resulting in an exothermic reaction with gas formation.

$^1$H-NMR analysis of the reaction product showed a peak in the Al-Me region, which is indicative of the presence of intermediate products.

The reaction mixture was left to stir at room temperature for 20 hours.

The mixture was then heated to 105° C. (oil bath) for 45 minutes.

$^1$H-NMR analysis showed no significant changes in the composition of the reaction mixture. No formation of aluminoxanes was observed.

Comparative Example 2

Benzyl Alcohol as Reactant

A 30 ml glass vial equipped with a magnetic stirring bar was charged with 6.1 g toluene and 2.7 g (37.5 mmol) trimethylaluminium (ex AkzoNobel). To this solution, 0.81 g (7.5 mmol) of benzyl alcohol (ex Baker) was slowly added, resulting in an exothermic reaction with gas formation.

$^1$H-NMR analysis of the reaction product showed a peak in the Al-Me region, which is indicative of the presence of intermediate products. The reaction mixture was left to stir at room temperature for 20 hours. The mixture was then heated to 105° C. (oil bath) for 45 minutes. $^1$H-NMR analysis showed no significant changes in the composition of the reaction mixture. No formation of aluminoxanes was observed.

Example 3

Prenol as Reactant with a Heating Step

A 30 ml glass vial equipped with a magnetic stirring bar was charged with 6.1 g toluene and 2.7 g (37.5 mmol) trimethylaluminium (ex AkzoNobel). To this solution, 0.66 g (7.5 mmol) of prenol (Sigma-Aldrich) was slowly added, resulting in an exothermic reaction with gas formation.

$^1$H-NMR analysis of the reaction product after dosing showed lots of small peaks in the Al-Me region, which is indicative of the presence of intermediate products.

The reaction mixture was left to stir at room temperature for 20 hours.

The mixture was then heated to 105° C. (oil bath) for 45 minutes.

¹H-NMR analysis showed that the small intermediate peaks disappeared and showed the formation of a broad signal next to the TMAL peak, confirming methylaluminoxane formation.

Example 4

Prenol as a Reactant

A 1,000 ml double-walled glass reactor equipped with an overhead stirrer was charged with 683.72 g of toluene. Next, 27.28 g (379 mmol) of trimethylaluminium (ex AkzoNobel) were added.

Over a period of 1 hour, 6.52 g (76 mmol) of prenol (Sigma-Aldrich) dissolved in 20 g toluene were evenly added. An exothermic reaction occurred and methane gas was evolved. The reaction mixture was kept at 25° C. during the prenol dosing using a Julabo temperature control system. When all the prenol was dosed, the reaction mixture was stirred for 22 hours at 25° C. Next, the excess of trimethylaluminium and toluene was flashed off using Büchi rotavapor set at a pressure of 139 mbar and using an oil bath set at 80° C. The trimethylaluminium/toluene was flashed off until a concentrated solution of 18 g was obtained. GC analysis of hydrolyzed samples showed only traces of prenol.

¹H-NMR confirmed the formation of methylaluminoxanes.

Example 5

Prenol as Reactant in the Presence of Aluminoxane as Catalyst

A 250 ml double-walled glass reactor equipped with an overhead stirrer was charged with 113 g toluene.

The reactor content was cooled to 18° C. using a Julabo temperature control system.

To the toluene 32.66 g (454 mmol) trimethylaluminium (ex AkzoNobel) were added.

Next, a catalytic amount of methylaluminoxane was added (17.5 g, 7 wt. % Al). When the temperature was stabilized, prenol (Sigma-Aldrich) was dosed at a rate of 0.165 ml/min using a HPLC pump. During the dosing of the prenol an exothermic reaction occurred and methane gas was evolved. The reaction mixture was maintained at c. 25° C.

Over a period of 210 minutes a total amount of 29.30 g (340 mmol prenol, 0.75 eqv.) prenol was dosed.

The reaction mixture was left to stir for 24 hours at 25° C.

GC analysis of hydrolyzed samples showed only traces of prenol. ¹H-NMR confirmed the formation of methylaluminoxanes.

Example 6

Prenol as Reactant with Dosing to Aluminoxane

A 250 ml double-walled glass reactor equipped with an overhead stirrer was charged with 115 g toluene.

The reactor content was cooled to 18° C. using a Julabo temperature control system.

Next 32.66 g (454 mmol) trimethylaluminium (ex AkzoNobel) were added.

When the temperature was stabilized, prenol (Sigma-Aldrich) was dosed at a rate of 0.154 ml/min using a HPLC pump. During the dosing of the prenol an exothermic reaction occurred and methane gas was evolved. The reaction mixture was maintained at c. 25° C.

Over a period of 210 minutes a total amount of 27.35 g (318 mmol prenol, 0.7 eqv.) prenol was dosed.

After all the prenol was dosed, the reaction mixture was dosed to 17.5 g of methylaluminoxane present in a second 250 ml double-walled glass reactor equipped with an overhead stirrer. During the dosing of the reaction mixture a second exothermic reaction occurred. The temperature of the reaction mixture in the second reactor was maintained at 25° C.

GC analysis of hydrolyzed samples after the dosing of the reaction mixture to methylaluminoxane showed only traces of prenol. ¹H-NMR confirmed the formation of methylaluminoxanes.

Example 7

Prenol as Reactant with Dosing of Aluminoxane

A 250 ml double-walled glass reactor equipped with an overhead stirrer was charged with 115 g toluene.

The reactor content was cooled to 18° C. using a Julabo temperature control system.

Next 32.66 g (454 mmol) trimethylaluminium (ex AkzoNobel) were added.

When the temperature was stabilized, prenol (Sigma-Aldrich) was dosed at a rate of 0.154 ml/min using a HPLC pump. During the dosing of the prenol an exothermic reaction occurred and methane gas was evolved. The reaction mixture was maintained at ca. 25° C.

Over a period of 210 minutes a total amount of 27.35 g (318 mmol prenol, 0.7 eqv.) prenol was dosed.

After all the prenol was dosed, the reaction mixture was cooled to −18° C. Next, 17.5 g methylaluminoxane were slowly dosed, with the temperature of the reaction mixture being maintained below −16° C.

Next, the reaction mixture was pumped through a heated spiral (I.D. 2.8 mm, int. volume c. 8 ml) of 70° C. at a rate of c. 4 ml/min., resulting in an exothermic reaction in the spiral. The reaction mixture coming out of the spiral was collected and cooled down to 25° C.

GC analysis of hydrolyzed samples after pumping the reaction mixture through the heated spiral showed only traces of prenol. ¹H-NMR confirmed the formation of methylaluminoxanes.

Example 8

Continuous Process with Prenol as Reactant and Continuous Dosing to Aluminoxane A solution of 22.1 wt. % trimethylaluminium in toluene was made by dissolving 146.97 g (2.041 mol) trimethylaluminium (AkzoNobel) in 519.03 g toluene (Baker).

A 30 ml double-walled glass reactor (reactor 1) equipped with an overhead stirrer was filled with 24 g of the trimethylaluminium solution.

The solution was cooled to 10° C. and prenol (SigmaAldrich) was dosed at a rate of 296 ml/minute.

Meanwhile a second 30 ml double-walled glass reactor (reactor 2), equipped with an overhead stirrer and an overflow draining line connected to a receiving flask, was filled with 25 g of a previously made methylaluminoxane (7 wt. % Al) solution in toluene (AkzoNobel).

After 17 minutes, when 4.31 g (50 mmol) prenol had been dosed, the trimethylaluminium solution was dosed to reactor 1 at a rate of 100 ml per hour. Simultaneously the content of reactor 1 was dosed to the PMAO solution in reactor 2 at such a rate that the liquid level in reactor 1 stayed constant. The temperature in reactor 2 was kept at c. 25° C.

The methylaluminoxane that was continuously made in reactor 2 was collected in a receiving flask via the overflow draining line.

Example 9

Geraniol as Reactant with Heating Step

A 30 ml glass vial equipped with a magnetic stirring bar was charged with 6.1 g toluene and 2.7 g (37.5 mmol) trimethylaluminium (ex AkzoNobel). To this solution, 4.05 g (26.3 mmol) of geraniol (Sigma-Aldrich) were slowly added, resulting in an exothermic reaction with gas formation. $^1$H-NMR analysis of the reaction product after dosing showed lots of small peaks in the Al-Me region, which is indicative of the presence of intermediate products.

The reaction mixture was left to stir at room temperature for 20 hours. The mixture was then heated to 105° C. (oil bath) for 45 minutes.

$^1$H-NMR analysis showed that the small intermediate peaks had disappeared and showed the formation of a broad signal next to the TMAL peak, confirming methylaluminoxane formation.

Example 10

Preparation of the Alkoxide Addition Product Intermediate with Prenol as Reactant A 250 ml double-walled glass reactor equipped with an overhead stirrer was charged with 26.0 g toluene. The reactor content was cooled to 18° C. using a Julabo temperature control system. To the toluene 26.1 g (363 mmol) trimethylaluminium (ex AkzoNobel) were added. When the temperature was stabilized, prenol (Sigma-Aldrich) was dosed at a rate of 0.175 ml/min using a HPLC pump. During the dosing of the prenol an exothermic reaction occurred and methane gas was evolved. The reaction mixture was maintained at 25° C. Over a period of 210 minutes a total amount of 31.24 g (363 mmol prenol, 1 eqv.) prenol was dosed.

Example 11

In-Situ Preparation of Supported Methylaluminoxane with Prenol as Reactant and Heating Step To a solution of alkoxide intermediate as prepared in Example 10, 0.43 mole eqv. trimethylaluminium was added. Next this mixture was dosed to a suspension of calcined silica in toluene. The suspension was heated until reflux. At c. 97° C., an exothermic reaction occurred, causing the reaction mixture to reflux. After 4 hours of refluxing, the reaction mixture was cooled to c. 100° C. and filtrated. The impregnated silica was washed twice with toluene and vacuum dried. Only traces of methylaluminoxane were found in the filtrate. SEM-EDX analysis showed a homogeneous distribution of aluminium through the silica particle.

Example 12

In-Situ Preparation of Supported Methylaluminoxane with Prenol as Reactant and Heating Step, with Dosing of the Carrier Before Adding the Alkylaluminium Compound To a suspension of calcined silica in toluene, alkoxide intermediate solution (6.3 mmol) as prepared in Example 10 was added. The suspension was left to stir for 1 hour. Next 0.41 mole eqv. trimethylaluminium was added. The suspension was heated until reflux. At c. 97° C., an exothermic reaction occurred, causing the reaction mixture to reflux. After 4 hours of refluxing, the reaction mixture was cooled to c. 100° C. and filtrated. The impregnated silica was washed twice with toluene and vacuum dried. No methylaluminoxane was found in the filtrate. SEM-EDX analysis showed a homogeneous distribution of aluminium through the silica particle.

Example 13

In-Situ Preparation of Supported Methylaluminoxane with Prenol as Reactant and Heating Step, Dosing of the Alkylaluminium Compound To a suspension of calcined silica in toluene, alkoxide intermediate solution as prepared in Example 10 was added. The suspension was heated until reflux. A mixture of (2.2 mole eqv. with regard to the first portion of the intermediate solution) and (1 mole eqv. with regard to the first portion of the intermediate solution) TMAL was slowly dosed to the refluxing suspension. After 4 hours of refluxing, the reaction mixture was cooled to c. 100° C. and filtrated. The impregnated silica was washed twice with toluene and vacuum dried. No methylaluminoxane was found in the filtrate.

Example 14

In-Situ Preparation of Supported Methylaluminoxane in the Presence of a Catalytic Amount of Methylaluminoxane and Heating Step Silica was suspended in toluene (Baker). In c. 10 minutes a PMAO solution (7.0 wt. % Al, 0.1 mole eqv. of the total targeted aluminium) was added to the suspension. The suspension was stirred for 1 hour. Next the product of Example 10 (previously made intermediate solution (0.72 mole eqv. of the total targeted aluminium)) and trimethylaluminium (0.18 mole eqv. of the total targeted aluminium) were added. The reaction mixture was stirred for 1 hour. After 1 hour of the stirring the suspension was heated until reflux. During the heating an exothermic reaction was observed. The suspension was refluxed for 4 hrs. Next the suspension was cooled to 100° C. The suspension was filtered over a 3 G glass fritted filter, washed twice with toluene, and dried.

Example 15

Comparison of Storage Stability of Supported and Non-Supported Aluminoxane

A sample of the aluminoxane prepared in Example 8 and of the silica-supported aluminoxane prepared in Example 13 were both stored for 3 weeks at 25° C. The viscosity of the aluminoxane increased and the silica supported aluminoxane showed no changes in physical behaviour.

The invention claimed is:

1. Process to prepare alkylaluminoxanes by reaction of alkylaluminium with a substituted allylic alcohol of the formula

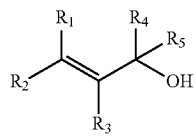

wherein each R1 and R2 independently are an aliphatic or aromatic hydrocarbon group, and R3, R4, and R5 each independently may be the same hydrocarbon group as R1 and R2 or a hydrogen atom in the presence of an inert organic solvent, wherein 0.1 to 0.8 molar equivalent of substituted allylic alcohol is used on 1 equivalent of alkylaluminium.

2. Process according to claim 1 wherein between 0.5 and 0.8 molar equivalent of substituted allylic alcohol is used on 1 equivalent of alkylaluminium.

3. Process according to claim 2 wherein between 0.6 and 0.75 molar equivalent of substituted allylic alcohol is used on 1 equivalent of alkylaluminium.

4. Process according to claim 1 wherein each R1 and R2 independently are a branched or unbranched alkyl or alkylene group of up to 20 carbon atoms, and wherein R3, R4, and R5 each independently may be the same alkyl or alkylene group as R1 and R2, or a hydrogen atom.

5. Process according to claim 1 wherein the substituted allylic alcohol is selected from the group of 4-methyl-3-pentene-2-ol, 3-methyl-2-pentene-1-ol, 3-methyl-2-hexene-1-ol, 3-ethyl-2-pentene-1-ol, (trans)-3,7-dimethyl-2,6-octadien-1-ol, and 3-methyl-2-butene-1-ol.

6. Process according to claim 1 wherein the alkylaluminium is a trialkylaluminium wherein the alkyl groups are alkyl groups of up to 8 carbon atoms.

7. Process of claim 6 wherein one or more of the alkyl groups on the alkylaluminium are isobutyl, ethyl or methyl.

8. Process according to claim 1 wherein the alkylaluminium is a compound wherein at least 50% of the alkyl groups are methyl.

9. Process according to claim 1 wherein the alkylaluminium contains trimethylaluminium.

10. Process according to claim 1 wherein the organic solvent is selected from the group of alkanes, such as heptanes or hexanes, or aromatics, such as toluene, xylene, ethylbenzene, cumene, or mesitylene.

11. Process according to claim 1 wherein the reaction of alkylaluminium with a substituted allylic alcohol is performed in the presence of an aluminoxane.

12. Process according to claim 1 wherein the inert organic solvent contains a carrier.

13. Process of claim 12 wherein the carrier is selected from the group of silica, magnesia, titania, zirconia, montmorillonite, phyllosilicate, alumina, silica-alumina, silica-chromium, silica-titania, magnesium chloride, graphite, magnesia, titania, zirconia, and combinations thereof.

14. Product obtainable by the process of any one of claim 1.

15. Use of the product of claim 14 as a catalyst component in a catalyst used in an olefin polymerization or oligomerization process.

* * * * *